United States Patent
Wilson

(10) Patent No.: US 9,310,313 B1
(45) Date of Patent: Apr. 12, 2016

(54) DIFFRACTIVE IMAGING OF GROOVE STRUCTURES ON OPTICAL TAPE

(71) Applicant: Oracle International Corporation, Redwood City, CA (US)

(72) Inventor: Scott D. Wilson, Thornton, CO (US)

(73) Assignee: Oracle International Corporation, Redwood City, CA (US)

( * ) Notice: Subject to any disclaimer, the term of this patent is extended or adjusted under 35 U.S.C. 154(b) by 0 days.

(21) Appl. No.: 14/584,609

(22) Filed: Dec. 29, 2014

(51) Int. Cl.
*G01N 21/00* (2006.01)
*G01N 21/898* (2006.01)
*G01N 21/956* (2006.01)

(52) U.S. Cl.
CPC ............ *G01N 21/898* (2013.01); *G01N 21/956* (2013.01)

(58) Field of Classification Search
CPC .............. G01N 21/89; G01N 21/8916; G01N 21/8901; G01N 21/8903; G01N 21/8806; G01N 21/956; G01N 21/898; G01N 21/94; G01N 2021/8472; G01N 21/88; G01N 2021/8887; G01N 21/474; G01N 21/55; G01N 21/86
See application file for complete search history.

(56) References Cited

U.S. PATENT DOCUMENTS

| | | | | |
|---|---|---|---|---|
| 4,933,566 A | * | 6/1990 | Masaaki | G01N 21/89 250/559.36 |
| 5,357,335 A | * | 10/1994 | Sparks | G01N 21/8903 356/237.2 |
| 5,383,776 A | * | 1/1995 | Trail | G01N 21/64 250/338.1 |
| 6,160,625 A | * | 12/2000 | Damer | G01N 21/896 250/559.06 |
| 2004/0066502 A1 | * | 4/2004 | Ohtsu | G01B 11/167 356/32 |

* cited by examiner

Primary Examiner — Michael P Stafira
(74) Attorney, Agent, or Firm — Brooks Kushman P.C.

(57) ABSTRACT

A groove-monitoring system for imaging an optical tape surface is provided. The optical tape surface includes a plurality of groove patterns embossed thereon. The groove-monitoring system includes an optical sensor, a first light source directing a first light beam onto the optical tape surface with a first angle of incidence such that the first light beam is directly reflected from the optical tape surface and imaged by the optical sensor. The groove-monitoring system also includes a second light source directing a second light beam onto the optical tape surface with a second angle of incidence such that the second light beam is diffracted from the optical tape surface and imaged by the optical sensor as a diffracted light image.

20 Claims, 12 Drawing Sheets

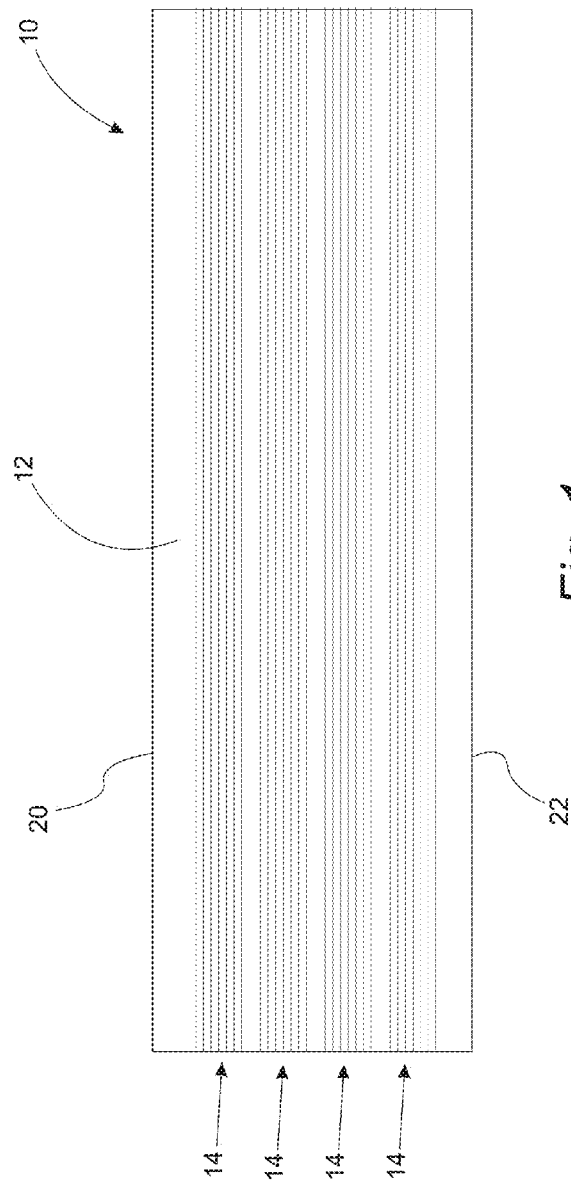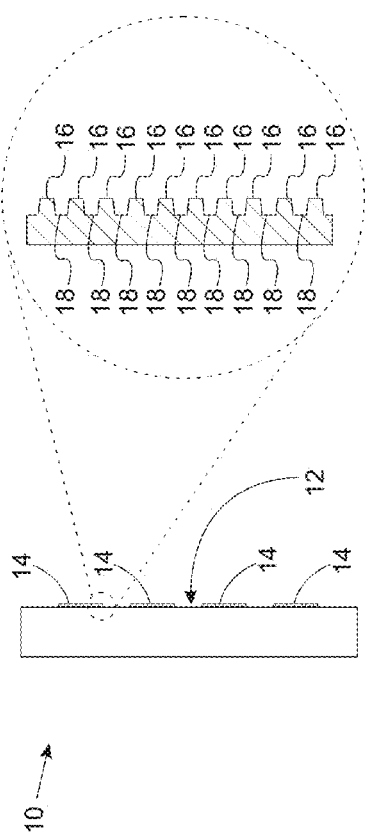

DIFFRACTIVE IMAGING OF GROOVE STRUCTURES ON OPTICAL TAPE

TECHNICAL FIELD

In at least one embodiment, the present invention relates to optical storage media such as optical storage tapes.

BACKGROUND

Optical recording media is a digital storage media onto which patterns are marked and read by light, typically from a laser. Optical data recording media requires a grooved structure on which to place the recorded marks. The grooves, or "tracks" as they are referred to in optical recording, typically have sub-micron dimensions that are nearly impossible to see with standard optical microscopes. For example, grooves with about a 320 nanometer track pitch present the necessary surface features to a tracking servo system for its laser spot to lock onto while reading and writing data. The groove structure must have consistently high quality in order for the recording system to be reliable. One of the critical parameters for the grooves in optical tapes is that they remain tightly parallel to the edges of tape. Deviations from parallelism may occur if there are problems in the tape slitting process. Currently, there are no known instruments capable of simultaneously making an electronic image of both the groove pattern and the edges of optical tape.

FIGS. 1 and 2 illustrate a portion of a typical optical recording medium. FIG. 1 is a top view of an optical storage tape while FIG. 2 is a side view of an optical storage tape. Optical data storage tape 10 includes a nanostructure surface relief pattern embossed on surface 12 of the optical storage tape. The nanostructure includes bands 14 each of which include a plurality of tracks having lands 16 and grooves 18 embossed in the direction parallel to the face of optical data storage medium thereon in a preformatting process. Bands 14 are interposed between tape edges 20 and 22.

Optical tape has never been successfully commercialized so no known instruments exist for measuring groove pattern quality. Although certain diffractive based sensors do exist for the optical disk industry, this technology has never been extended to optical tapes.

Accordingly, there is a need for systems and method for accessing the parallelism in optical storage tapes.

SUMMARY

The present invention solves one or more problems of the prior art by providing, in at least one embodiment, a groove-monitoring system for imaging an optical tape surface having a plurality of groove patterns embossed thereon. The groove-monitoring system includes an optical sensor and a first light source directing a first light beam onto the optical tape surface with a first angle of incidence such that the first light beam is directly reflected from the optical tape surface and imaged by the optical sensor. The groove-monitoring system also includes a second light source directing a second light beam onto the optical tape surface with a second angle of incidence such that the second light beam is diffracted from the optical tape surface and imaged by the optical sensor as a diffracted light image. The invention generates images of groove-patterned areas on optical recording tape without the need for very high magnification instruments such as atomic force or scanning electron microscopes. The invention generates an image of the grooved areas by using light diffracted by grooves onto a high resolution sensor such as a CCD or CMOS imaging device. The invention makes possible the control and qualification of groove patterns on optical tape. For aiding the manufacture of optical tape, the invention may be used in a closed-loop tape slitting control system to ensure that tape edges and groove patterns meet parallelism requirements. In addition, the invention makes possible the monitoring of the consistency of groove patterns by identifying areas where voids (dropouts), debris or defects may exist. This can be done during the tape manufacturing process and in subsequent quality control testing by the tape drive manufacturer.

In another embodiment, a groove-monitoring system for imaging an optical tape surface that includes a plurality of groove patterns is provided. The groove-monitoring system includes a linear optical sensor array and a first light emitting diode providing a first light beam that is directed onto the optical tape surface with a first angle of incidence such that the first light beam is directly reflected from the optical tape surface and imaged by the linear optical sensor array as a direct reflection image. The groove-monitoring system also includes a second light emitting diode directing a second light beam onto the optical tape surface with a second angle of incidence such that the second light beam is diffracted from the optical tape surface and imaged by the linear optical sensor array as a diffracted light image. A tape guide holds the optical tape proximate to the first light source and the second light source such that the first light source and the second light source direct light onto the tape surface. The groove monitoring system also includes a tape drive subsystem for moving the optical tape in front of the first light source and the second light source. Characteristically, the tape drive subsystem moves the optical tape over the tape guide.

In another embodiment, a method for imaging an optical tape surface that includes a plurality of grooves patterns is provided. The method includes a step of directing a first light beam onto the optical tape surface at a first angle of incidence to produce directly reflected light from the optical tape surface. A second light beam is directed onto the optical tape surface at a second angle of incidence to produce diffracted light from the optical tape surface. Advantageously, the directly reflected light is imaged as a direct reflection image and the diffracted light is imaged as a diffracted light image.

BRIEF DESCRIPTION OF THE DRAWINGS

FIG. 1 provides a top view of an optical storage tape;

FIG. 2 is a side view of an optical storage tape;

DETAILED DESCRIPTION

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: the description of a group or class of materials as suitable or preferred for a given purpose in connection with the invention implies that mixtures of any two or more of the members of the group or class are equally suitable or preferred; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Figure 3:
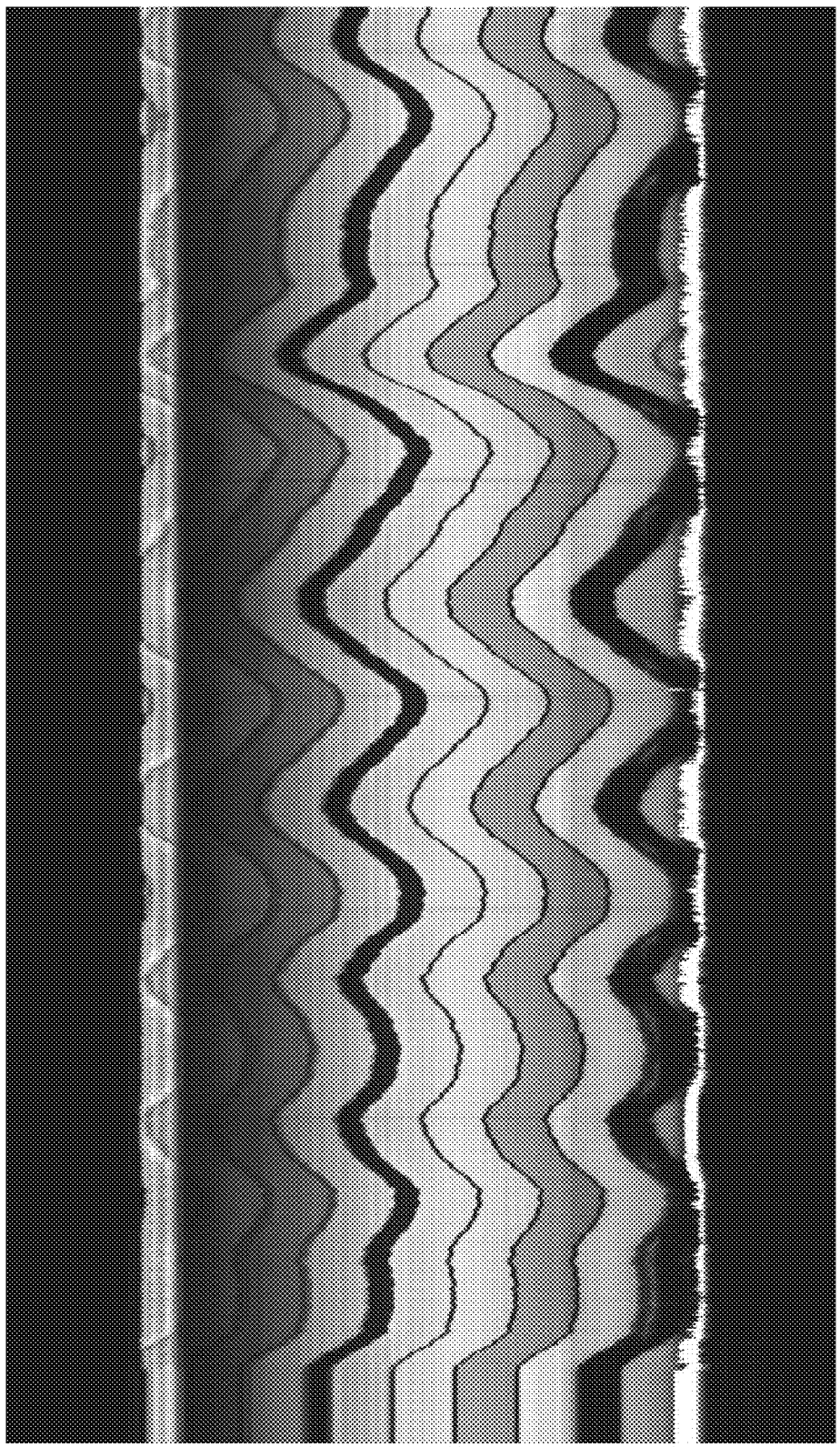
FIG. 3 provides a two dimensional bitmap image taken by the groove-monitoring system of a tape having extreme groove pattern wander.

In an embodiment, a groove-monitoring system for imaging an optical tape that includes a plurality of grooves is provided. The groove-monitoring system includes a mechanical housing, light emitting diodes (LEDs), lenses and a linear optical sensor array. The components are arranged in a unique geometry such that the semi-monochromatic light emitted from an LED is diffracted from the groove structure, gathered by lenses and imaged onto the optical sensor to yield an electronic image of the groove pattern. Additionally, a second LED is used to reflect light from the edges of tape to include the tape edges in the resulting composite image. The invention also uses a tilted plane optical imaging method where both the object plane (i.e., an optical storage tape) and the image plane (optical sensor array) are tilted with respect to the camera's optical axis. This is to maintain good focus across the camera's field of view while its optical axis is angled relative to the tape surface. FIG. 3 provides a two dimensional bitmap image taken by the groove-monitoring system of a tape having extreme groove pattern wander. The image consists of 4000 consecutive line scans. In this example, the tape velocity is 2 meters per second and the scan rate is 125 lines/sec.

Figure 4:
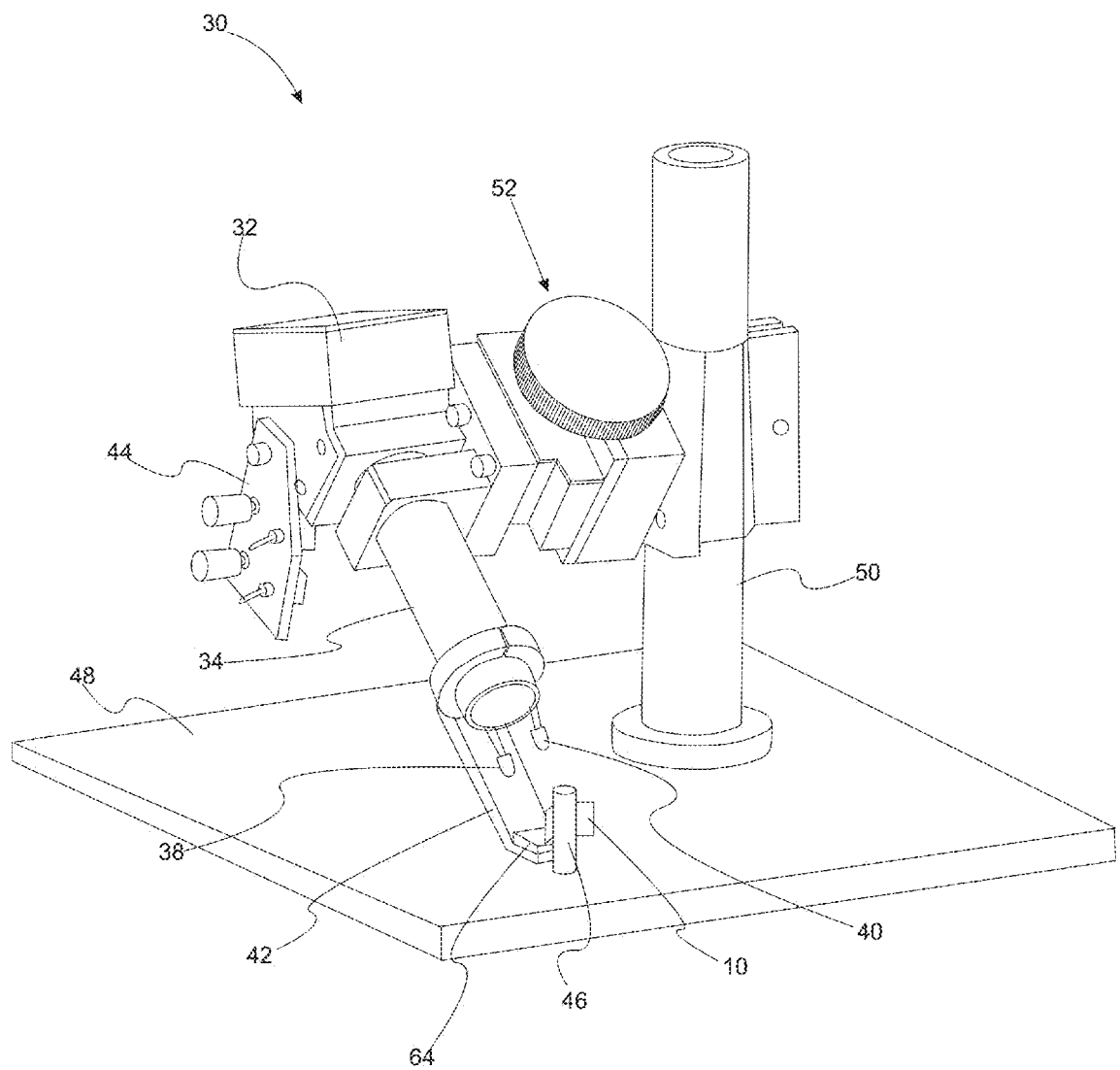
FIG. 4 is a perspective view of the groove-monitoring system for accessing parallelism of grooves in an optical storage tape.
Figure 5:
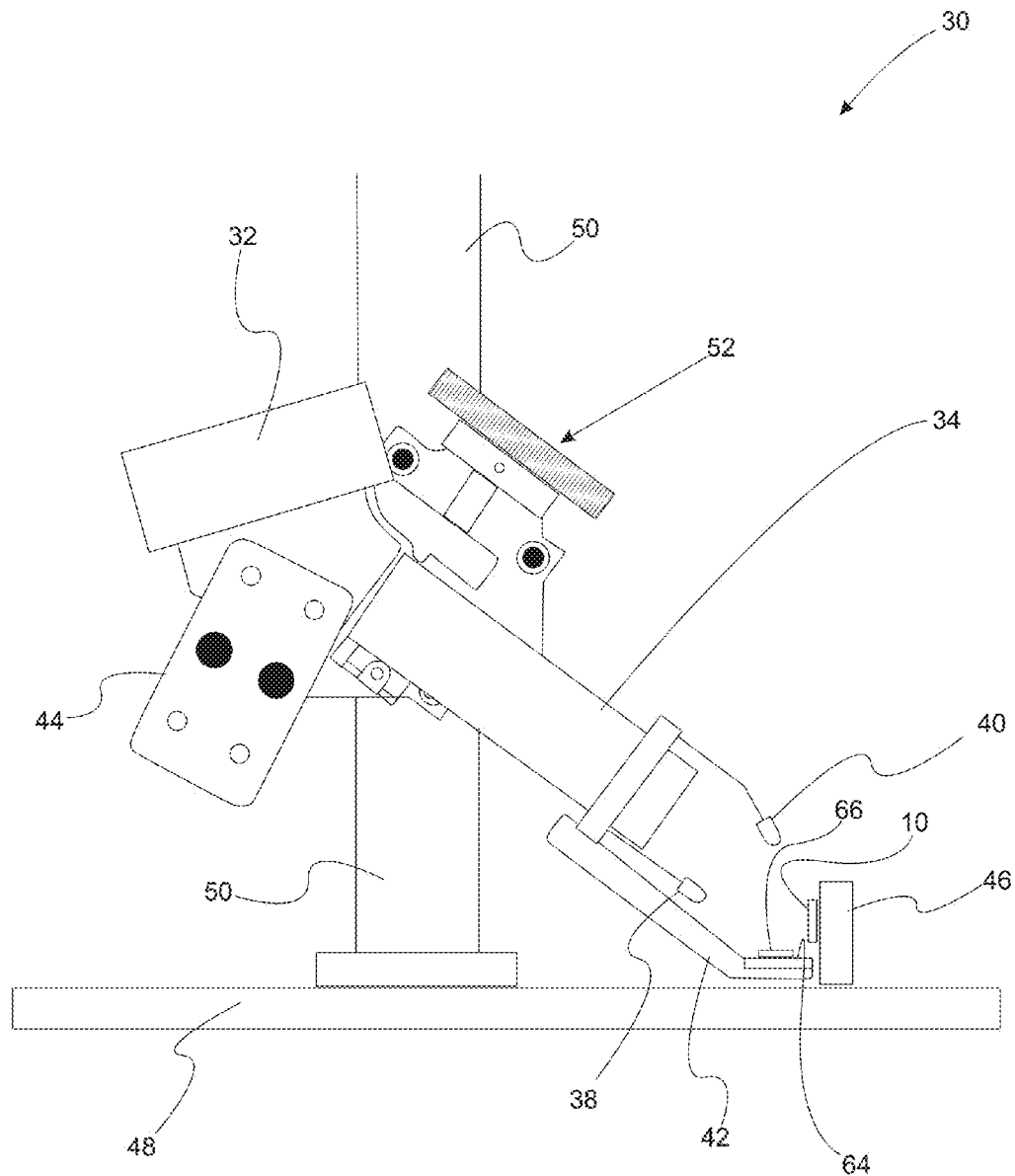
FIG. 5 is a schematic side view of a groove-monitoring system for accessing parallelism of grooves in an optical storage tape.
Figure 6:
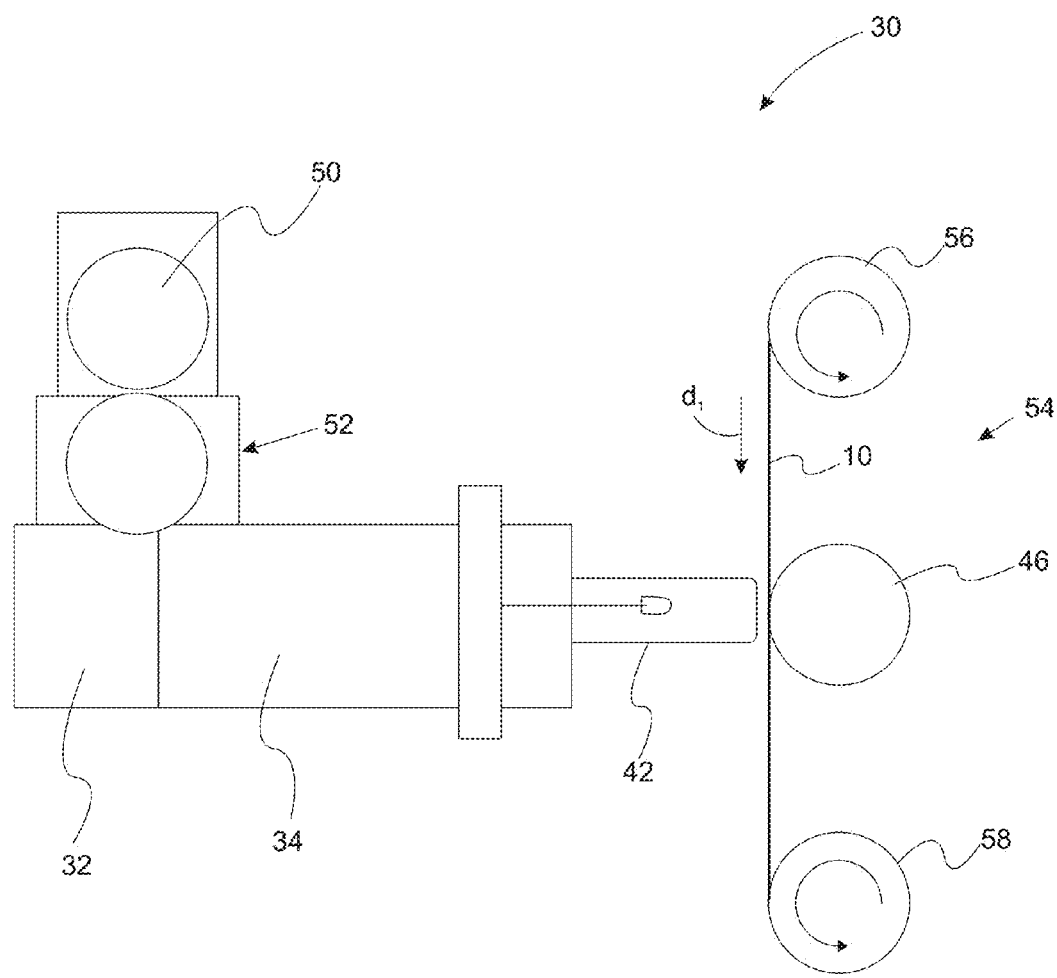
FIG. 6 is a schematic top view of a groove-monitoring system for accessing parallelism of grooves in an optical storage tape.

With reference to FIGS. 4, 5, and 6, a groove-monitoring system for imaging an optical tape that includes a plurality of grooves is schematically illustrated. FIG. 4 is a perspective view of the groove-monitoring system. FIG. 5 is a schematic side view of a groove-monitoring system. Groove-monitoring system 30 includes optical sensor 32 which is connected to a lens system such as lens tube 34. Lens tube 34 collects light reflected and/or diffracted from the surface of tape 10. Tape 10 is of the general design set forth in FIGS. 1 and 2 which includes bands of tracks having lands 16 and grooves 18. Light sources 38 and 40 are the sources of light that is reflected and/or diffracted from the surface of tape 10. In a refinement, light sources 38 and 40 provide light having a mean wavelength from 300 to 700 nanometers. In another refinement, the light is monochromatic or nearly monochromatic. In this context, nearly monochromatic means that the distribution of wavelengths has a mean wavelength from 300 to 700 nanometers and a standard deviation from about 50 to 100 nanometers. In a refinement, light sources 38 and 40 are each independently light emitting diodes. Light sources 38 and 40 which are mounted on light source mount/mirror paddle 42 illuminate the surface of tape 10 and independently have their own intensity and ON/OFF controls mounted in light source control system 44. In a refinement, the light sources get their power from the camera's USB cable. Tape guide 46 holds tape 10 in position proximate to the light sources such that light emitting diodes 38 and 40 direct light onto the tape surface. In a refinement, tape guide 46 is a set of twin bump stabilizers which advantageously prevent curling of the edges of the tape. The reflected and/or diffracted light is collected by optical sensor 32. System 30 is mounted onto surface 48 by mount 50 in front of the tape path. Rack and pinion stage 52 allows adjustment of the positions of the optical components—optical sensor 32, lens tube 34, light source 38, and light source 40 and to achieve best focus.

Still referring to FIGS. 4, 5, and 6, groove-monitoring system 30 also includes tape drive subsystem 54 for moving tape 10 in front of the light sources and image acquiring components (e.g., optical sensor 32). Tape drive subsystem 54 includes feed spool 56 which provides optical tape to the motor driven pickup spool 58 while the tape moves along direction $d_1$ and passes over tape guide 46. Although tape drive subsystem 54 may move the tape with virtually any speed, a tape speed of 0.5 to 20 meters/second is typical.

Figure 7:
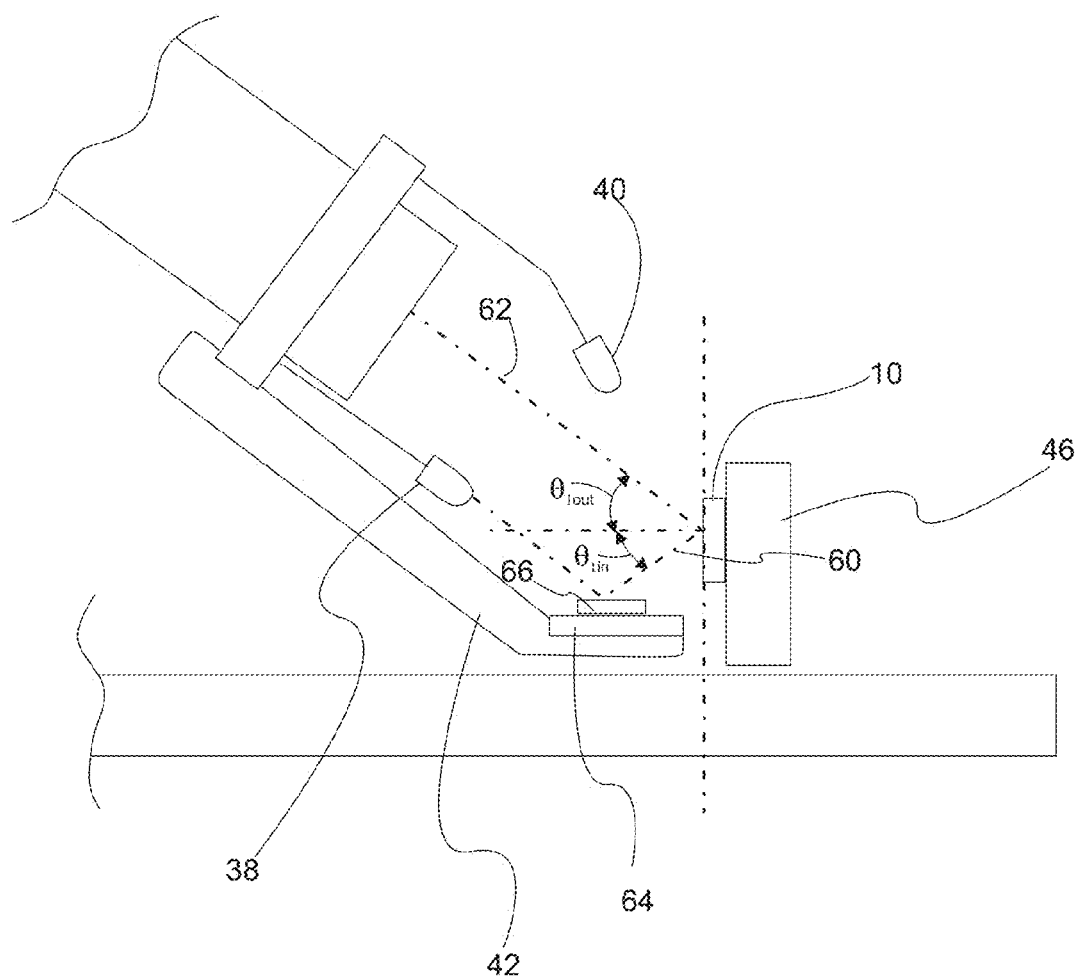
FIG. 7 is a schematic side view of a groove-monitoring system collecting a direct reflection image of an optical tape surface.
Figure 8:
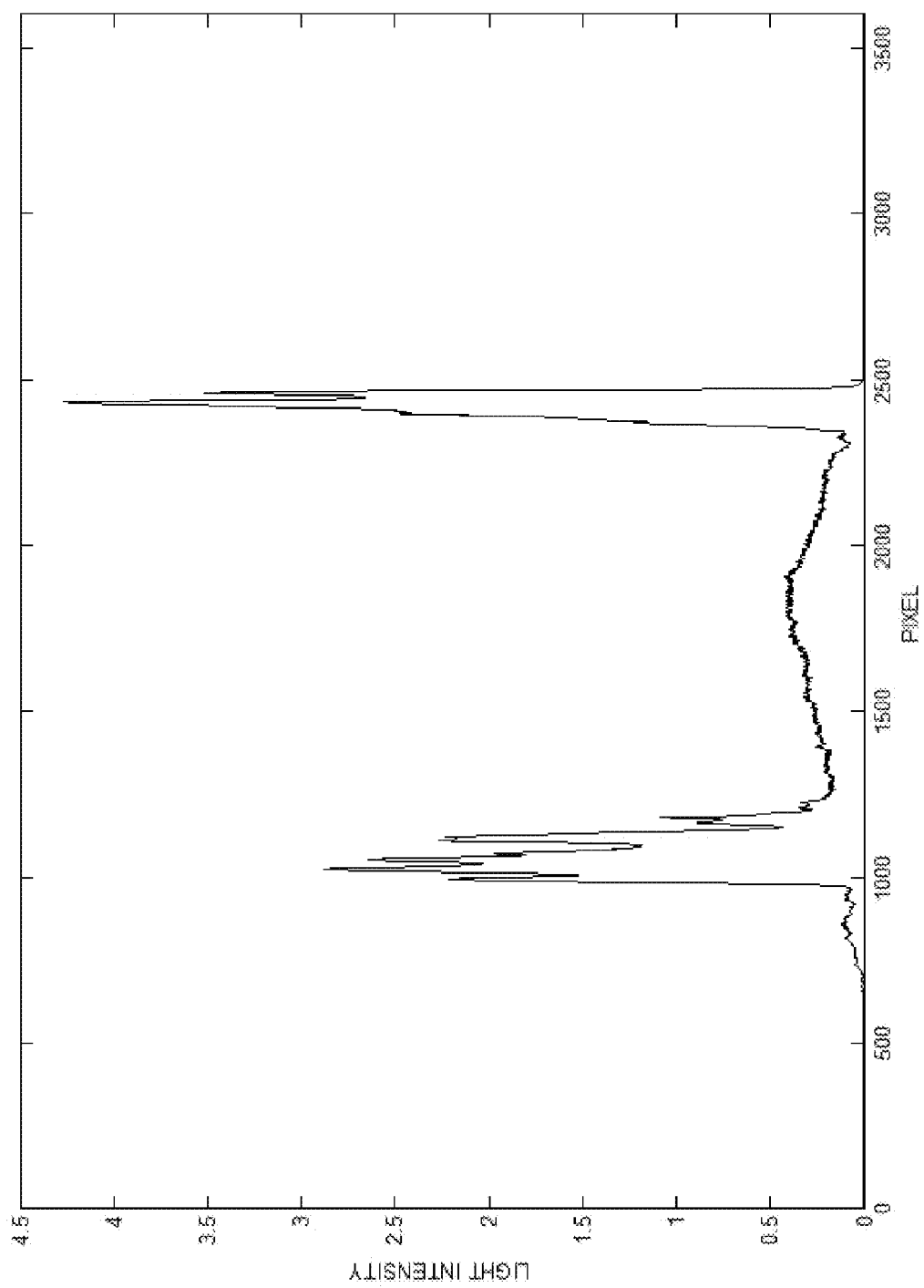
FIG. 8 provides an image of the directly reflected light from the tapes edges.

With reference to FIG. 7, light source 38 illuminates tape 10 with a first light beam 60 at a first angle of incidence $\theta_{1in}$ to generate an image of the tape surface by direct reflection. As depicted in FIG. 7, light source 38 illuminates tape 10 from below. Since the tape is visualized by direct reflection, $\theta_{1in}$ equals the angle of reflection $\theta_{1out}$ of reflected light beam 62. Light emitted from light source 38 reflects off of mirror 64 onto the tape surface. Mirror 64 is mounted on light source mount/mirror paddle 42 which is attached to lens tube 34. The primary purpose of this mode of imaging is to "see" the tape's edges so that lateral tape motion (LTM) can be delineated from a measurement of groove pattern wander. In a refinement, a non-reflecting mask 66 (e.g., a black mask) is placed on the mirror to block a portion of the light reflected off of mirror 64 so that only the tape edges appear in the resulting direct reflection image. Blocking a portion of mirror 52 enhances imaging of the grooves by optical sensor 32. FIG. 8 provides an image of the directly reflected light from the tapes edges with light source 38 turned on and light source 40 turned off.

Figure 9:
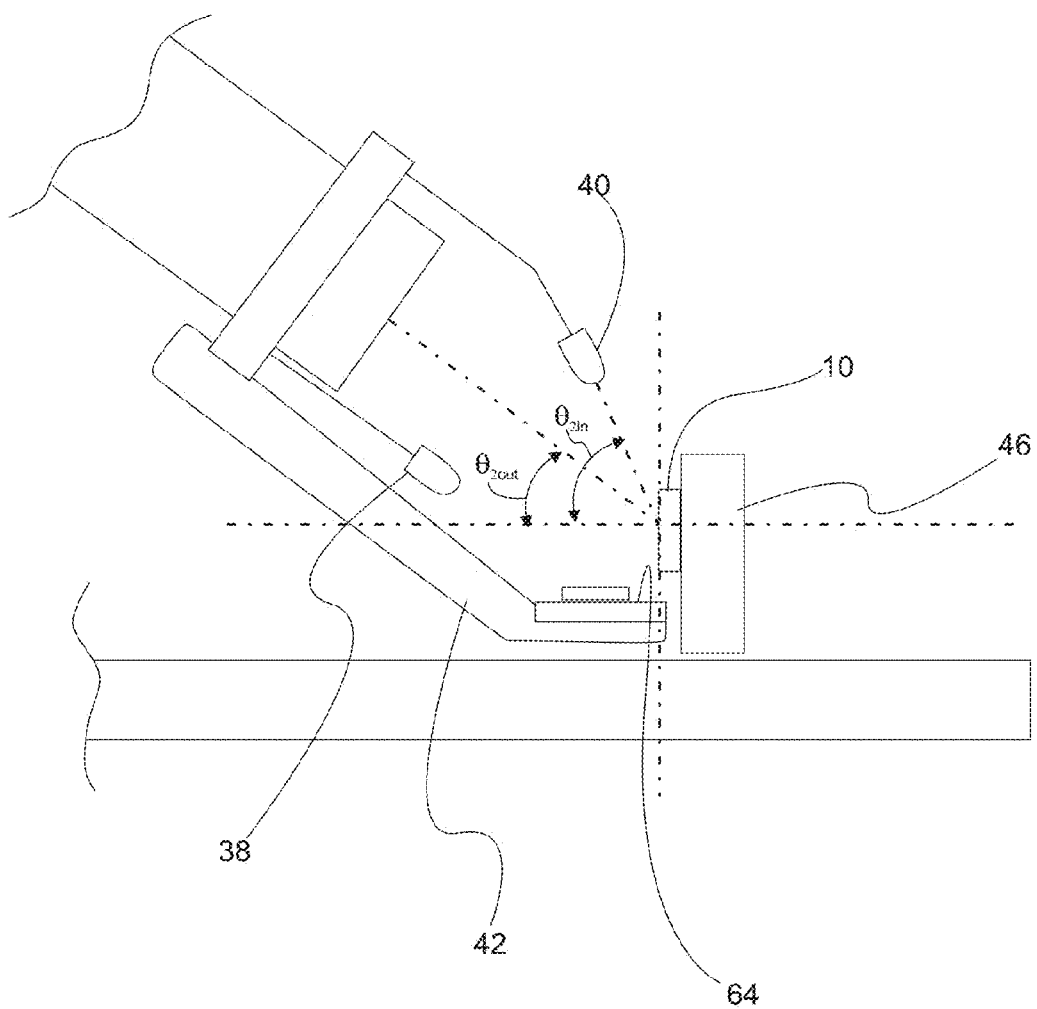
FIG. 9 is a schematic side view of a groove-monitoring system collecting a diffracted image of an optical tape surface.
Figure 10:
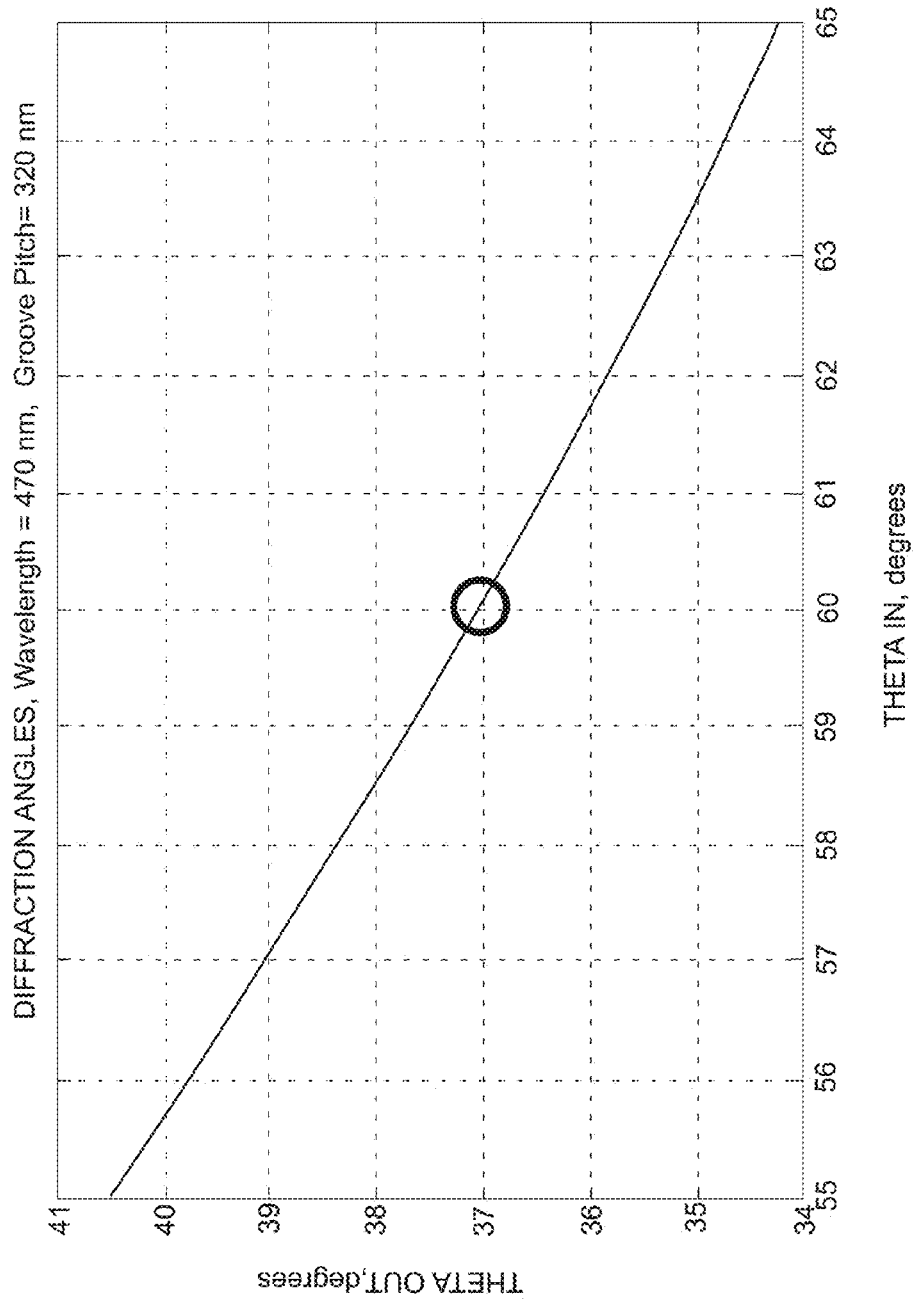
FIG. 10 is a plot of the diffraction angle versus angle of incidence in accordance to Formula I.
Figure 11:
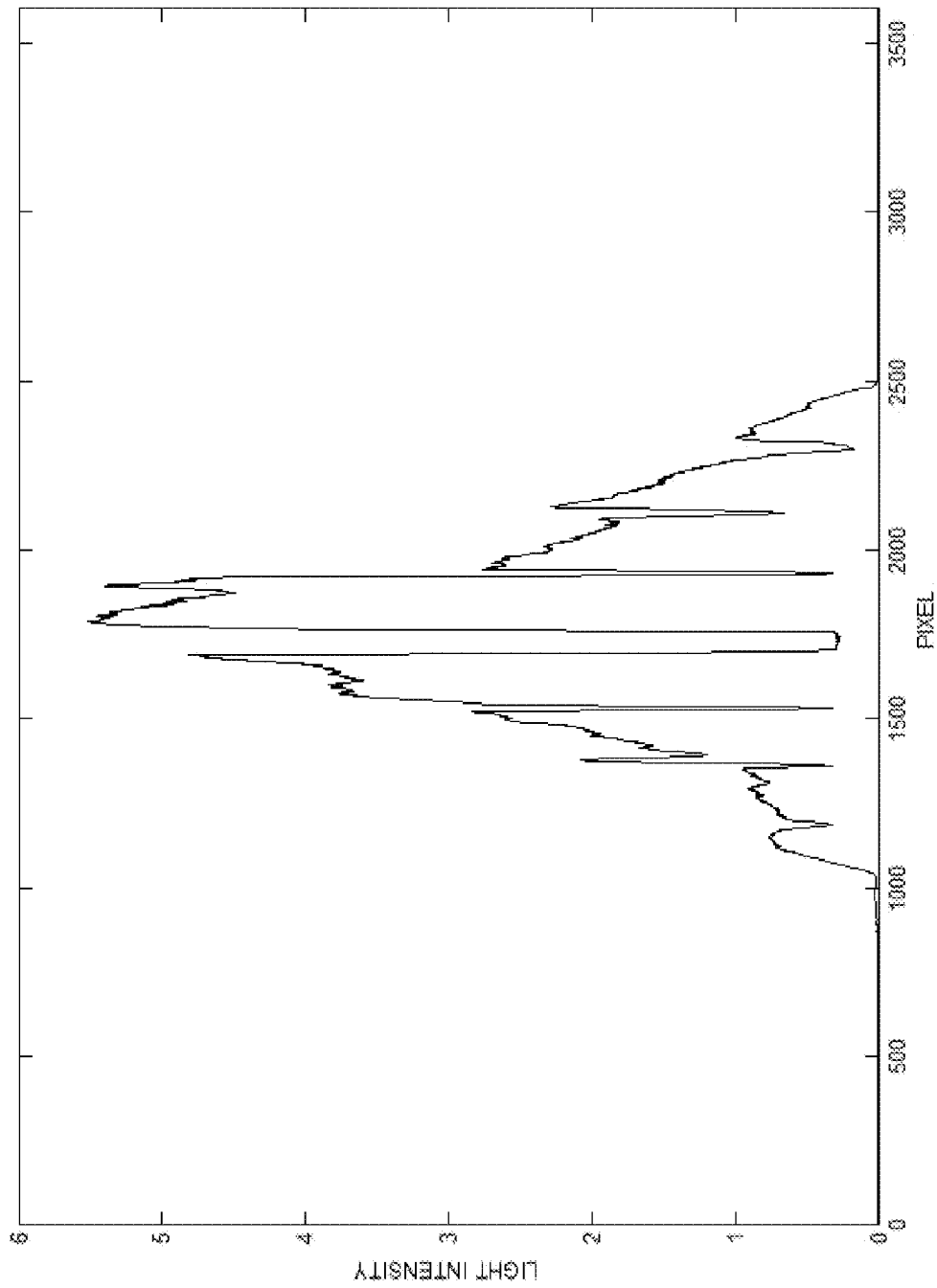
FIG. 11 provides an image of the diffracted light from the optical tape groove patterns.
Figure 12:
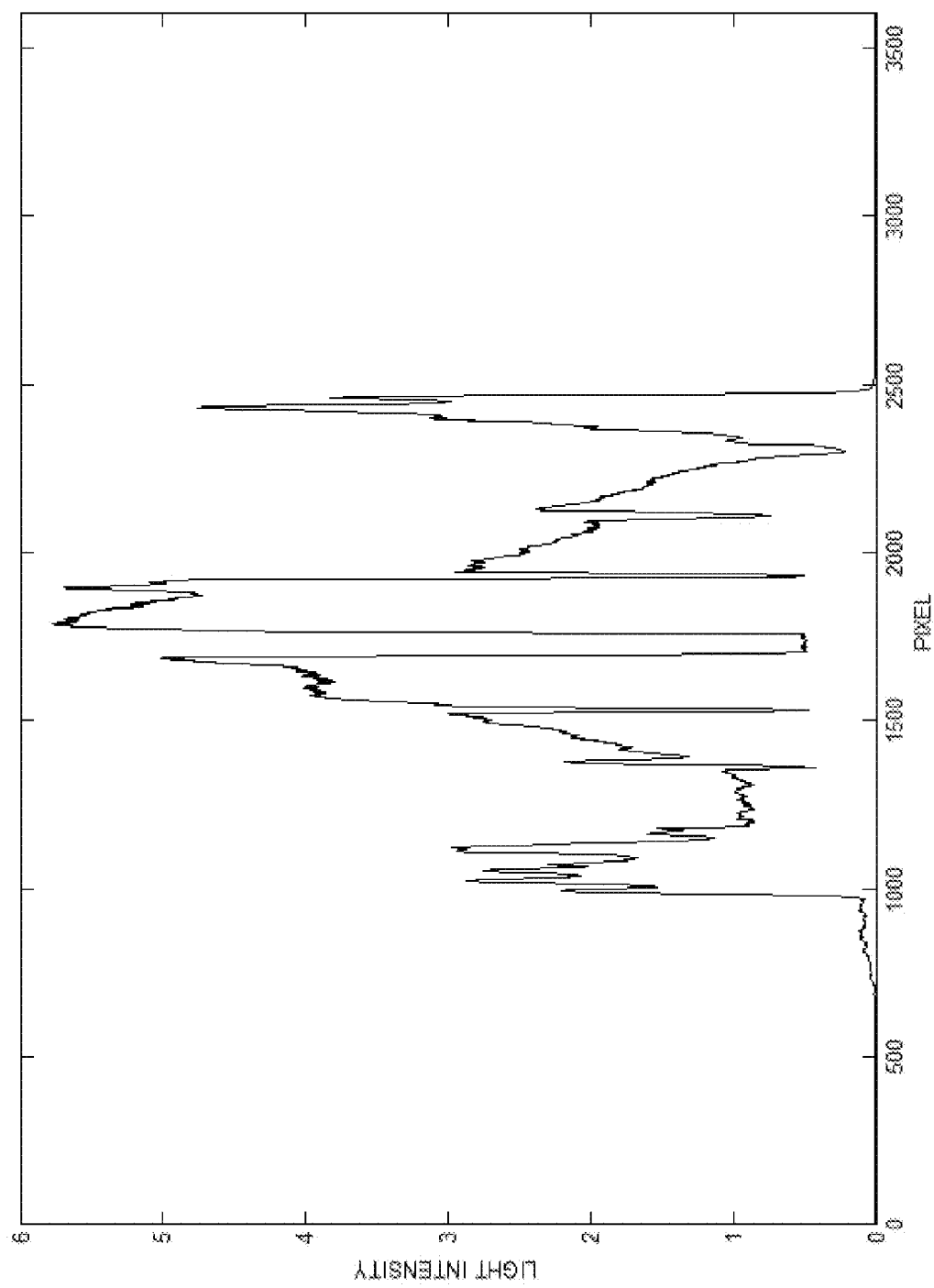
FIG. 12 provides a simultaneous image of directly reflected light from the tape edges and the diffracted light from the optical tape groove patterns.

With reference to FIG. 9, light source 40 illuminates the surface of optical tape 10 with a second angle of incidence $\theta_{2in}$. FIG. 7 depicts light source 40 illuminating the tape from above to generate an image of the groove pattern via diffraction. The well-known formula for diffraction from a grating is provided by formula I:

$$\sin(\theta_{2in}) + \sin(\theta_{2out}) = n\lambda/\Lambda \qquad \text{I}$$

where $\theta_{2in}$ is first angle of incidence, $\theta_{2out}$ is the diffracted (output) angle, $\lambda$ is the mean wavelength of the second light source, $\Lambda$ is the grating period (track pitch) and n is the diffraction order (=1). As shown in FIG. 9, $\theta_{2in}$ is the angle between the ray of light incident on the tape surface and a line perpendicular to the tape surface and $\theta_{2out}$ is the angle between a perpendicular line to the tape surface and the line from the position of the light incident to the tape surface to the light sensor. The intensity of light is desirably a maximum at the $\theta_{2out}$. FIG. 10 provides a plot of the output vs. input angles for $\lambda$=470 nm and $\Lambda$=320 nm. For example, the output angle can be 37° so the angle of incidence for light emitting diode 48 can be about 60°. Since LED radiance patterns are fairly broad, the incidence angle need not be precise in order to obtain a good diffraction image. When the system is properly aligned and with only light source 40 being active, an image similar to FIG. 11 is obtained. Finally, FIG. 12 provides a simultaneous image of directly reflected light from the tapes edges and the diffracted light from the optical tape groove patterns.

As set forth above, groove-monitoring system 30 includes optical sensor 32. In a refinement, optical sensor 32 is a linear optical sensor array. An example of a particularly useful optical sensor is the MIGHTEX® line scan camera commercially available from Mightex Systems. Characteristically, this camera captures images with a 1×3,600 pixel image sensor at scan rates of up to 125 lines per second. Moreover, the software packaged with the MIGHTEX® line scan camera provides real-time viewing of line scans on a computer monitor similar to an oscilloscope display, continuous imaging or externally triggered single line scans, wide range of exposure control, and frame-grabbing capability for storing single line scans or composite bitmap (2-D) grayscale images on a PC for later evaluation.

Figure 13:
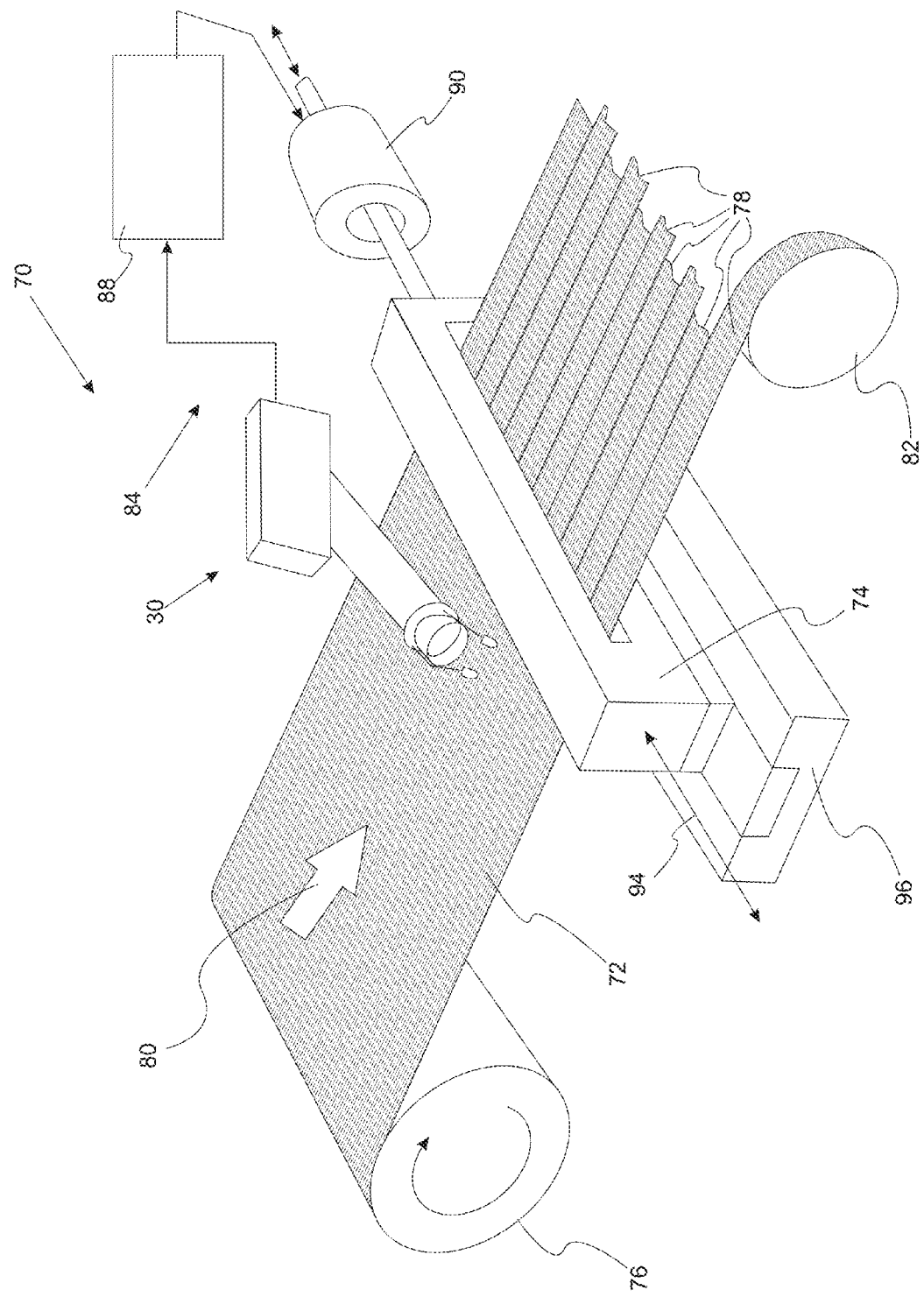
FIG. 13 is a schematic illustration of a closed loop tape slitting control system is provided.

With reference to FIG. 13, a schematic illustration of a closed loop tape slitting control system is provided. Tape slitting system 70 includes groove-monitoring system 30 as set forth above. Optical jumbo tape 72 is provided to tape slitting mechanism 74 from optical tape jumbo roll 76. Tape slitting mechanism 74 includes a plurality of tape cutting blades that cut the optical tape into a plurality of strands 78. Optical jumbo tape 72 moves along direction 80 through tape slitting mechanism 76 to single strand tape rolls 82. Groove-monitoring system 30 monitors a grooved area of optical jumbo tape 72 to evaluate the degree to which the groove tracks are parallel during cutting through a feedback loop 84. The feedback loop 84 includes groove-monitoring system 30, control electronics 88, linear actuator 90, and tape slitting mechanism 76. Upon receiving information about the locations of the groove tracks from groove-monitoring system 30, the control moves tape slitting mechanism 72 via linear actuator 90 such that optical tape 72 is cut in a manner in which the tracks are parallel to the edges of the strands of optical tape. Linear actuator 90 moves optical tape 72 along direction 94 with the motion being guided by linear slide 96. Typically, the distance of this motion is small being less than 3 mm.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A groove-monitoring system for imaging an optical tape surface that includes a plurality of groove patterns, the groove-monitoring system comprises:
   an optical sensor;
   a first light source providing a first light beam that is directed onto the optical tape surface with a first angle of incidence such that the first light beam is directly reflected from the optical tape surface and imaged by the optical sensor as a direct reflection image; and
   a second light source directing a second light beam onto the optical tape surface with a second angle of incidence such that the second light beam is diffracted from the optical tape surface and imaged by the optical sensor as a diffracted light image.

2. The groove-monitoring system of claim 1 further comprising a lens system that collects light reflected and/or diffracted from the optical tape surface.

3. The groove-monitoring system of claim 1 wherein the first light source and the second light source are each independently a light emitting diode.

4. The groove-monitoring system of claim 1 wherein the first light source and the second light source each independently provide light having a mean wavelength from 300 to 700 nanometers.

5. The groove-monitoring system of claim 1 wherein the first light source and the second light source each independently provide monochromatic or semi-monochromatic light.

6. The groove-monitoring system of claim 1 wherein the first light source and the second light source each independently provide light having a mean wavelength from 300 to 700 nanometers and a standard deviation from about 50 to 100 nanometers.

7. The groove-monitoring system of claim 1 further comprising a tape guide that holds an optical tape proximate to the first light source and the second light source such that the first light source and the second light source direct light onto the tape surface.

8. The groove-monitoring system of claim 7 further comprising a tape drive subsystem for moving an optical tape in front of the first light source and the second light source, the tape drive subsystem moving the optical tape over the tape guide.

9. The groove-monitoring system of claim 1 further comprising a mirror that reflects light from the first light source onto the optical tape surface at the first angle of incidence.

10. The groove-monitoring system of claim 9 further comprising a non-reflecting mask that is placed on the mirror to block a portion of the mirror so that only tape edges appear in the direct reflection image.

11. The groove-monitoring system of claim 1 wherein the optical sensor is a linear optical sensor array.

12. The groove-monitoring system of claim 1 wherein the second angle of incidence is determined from formula I:

$$\sin(\theta_{2in}) + \sin(\theta_{2out}) = n\lambda/\Lambda \qquad (I)$$

where $\theta_{2in}$ is the second angle of incidence, $\theta_{2out}$ is the diffracted angle, $\lambda$ is the mean wavelength of the second light source, $\Lambda$ is the track pitch, and n is the diffraction order.

13. A groove-monitoring system for imaging an optical tape surface that includes a plurality of groove patterns, the groove-monitoring system comprises:

a linear optical sensor array;

a first light emitting diode providing a first light beam that is directed onto the optical tape surface with a first angle of incidence such that the first light beam is directly reflected from the optical tape surface and imaged by the linear optical sensor array as a direct reflection image; and a second light emitting diode directing a second light beam onto the optical tape surface with a second angle of incidence such that the second light beam is diffracted from the optical tape surface and imaged by the linear optical sensor array as a diffracted light image;

a tape guide that holds an optical tape proximate to the first light emitting diode and the second light emitting diode such that the first light emitting diode and the second light emitting diode direct light onto the tape surface; and a tape drive subsystem for moving an optical tape in front of the first light emitting diode and the second light emitting diode, the tape drive subsystem moving the optical tape over the tape guide.

14. The groove-monitoring system of claim 13 further comprising a lens system that collects light reflected and/or diffracted from the optical tape surface.

15. The groove-monitoring system of claim 13 wherein the first light emitting diode and the second light emitting diode each independently provide light having a mean wavelength from 300 to 700 nanometers.

16. The groove-monitoring system of claim 13 wherein the first light emitting diode and the second light emitting diode each independently provide monochromatic light.

17. The groove-monitoring system of claim 13 wherein the first light emitting diode and the second light emitting diode each independently provide light having a mean wavelength from 300 to 700 nanometers and a standard deviation from about 50 to 100 nanometers.

18. A method for imaging an optical tape surface that includes a plurality of grooves patterns, the method comprising:

directing a first light beam onto the optical tape surface at a first angle of incidence to produce directly reflected light from the optical tape surface;

directing a second light beam the optical tape surface at a second angle of incidence to produce diffracted light from the optical tape surface;

imaging the directly reflected light as a direct reflection image; and imaging the diffracted light as a diffracted light image.

19. The method of claim 18 wherein the first light beam and the second light beam each independently have a mean wavelength being from 300 to 700 nanometers and a standard deviation from about 50 to 100 nanometers.

20. The method of claim 19 wherein the directly reflected light and the diffracted light are each imaged with a linear optical sensor array.

* * * * *